United States Patent
Kim et al.

(10) Patent No.: US 10,487,024 B2
(45) Date of Patent: Nov. 26, 2019

(54) METAL-LOADED ZEOLITE CATALYST FOR DEHYDROGENATION OF LIGHT ALKANE AND PREPARATION METHOD THEREOF

(71) Applicant: Korea Research Institute of Chemical Technology, Daejeon (KR)

(72) Inventors: Jeong-Rang Kim, Daejeon (KR); Soo Jin Kwon, Seongnam-si (KR); Hyung Ju Kim, Sejong-si (KR)

(73) Assignee: Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 15/951,152

(22) Filed: Apr. 11, 2018

(65) Prior Publication Data

US 2018/0297913 A1    Oct. 18, 2018

(30) Foreign Application Priority Data

Apr. 13, 2017   (KR) .................. 10-2017-0047842

(51) Int. Cl.

| | | |
|---|---|---|
| *B01J 29/06* | (2006.01) | |
| *C07C 5/333* | (2006.01) | |
| *C07C 11/06* | (2006.01) | |
| *C07C 11/08* | (2006.01) | |
| *C07C 11/04* | (2006.01) | |
| *B01J 29/70* | (2006.01) | |
| *B01J 29/12* | (2006.01) | |
| *B01J 29/08* | (2006.01) | |
| *B01J 29/068* | (2006.01) | |
| *B01J 29/74* | (2006.01) | |
| *B01J 37/02* | (2006.01) | |
| *B01J 37/30* | (2006.01) | |

(52) U.S. Cl.
CPC ........... *C07C 5/3337* (2013.01); *B01J 29/061* (2013.01); *B01J 29/068* (2013.01); *B01J 29/088* (2013.01); *B01J 29/126* (2013.01); *B01J 29/7057* (2013.01); *B01J 29/7415* (2013.01); *B01J 37/0201* (2013.01); *B01J 37/30* (2013.01); *C07C 5/3332* (2013.01); *C07C 11/04* (2013.01); *C07C 11/06* (2013.01); *C07C 11/08* (2013.01); *B01J 2229/186* (2013.01); *C07C 2523/08* (2013.01); *C07C 2523/14* (2013.01); *C07C 2529/068* (2013.01); *C07C 2529/12* (2013.01); *C07C 2529/74* (2013.01)

(58) Field of Classification Search
CPC ...... B01J 29/061; B01J 29/068; B01J 29/126; B01J 29/088; B01J 29/7057; B01J 29/7415; B01J 2229/186; B01J 37/0201; B01J 37/30; C07C 2529/12; C07C 2529/74; C07C 2529/068; C07C 5/3337; C07C 5/3332; C07C 11/06; C07C 11/08; C07C 11/04; C07C 2523/08; C07C 2523/14

USPC ........... 502/60, 61, 73, 74, 79; 585/654, 660
See application file for complete search history.

(56) References Cited

U.S. PATENT DOCUMENTS

| | | | |
|---|---|---|---|
| 5,736,478 A * | 4/1998 | Cortright | B01J 29/61 502/74 |
| 6,486,370 B1 | 11/2002 | Rende et al. | |
| 6,756,515 B2 | 6/2004 | Rende et al. | |
| 6,797,850 B2 | 9/2004 | Kourtakis et al. | |
| 6,867,340 B2 * | 3/2005 | Oh | B01J 29/44 585/467 |
| 2003/0036670 A1 * | 2/2003 | Oh | B01J 29/22 585/400 |
| 2010/0216630 A1 * | 8/2010 | Gajda | B01J 23/62 502/73 |
| 2013/0129575 A1 * | 5/2013 | Lewis | F01N 3/106 422/170 |
| 2013/0256194 A1 * | 10/2013 | Serban | B01J 23/58 208/134 |
| 2013/0261363 A1 * | 10/2013 | Serban | B01J 23/63 585/430 |
| 2013/0296614 A1 * | 11/2013 | Kuechler | B01J 21/00 568/798 |

OTHER PUBLICATIONS

Concepcion et al., "The promotional effect of Sn-beta zeolites on platinum for the selective hydrogenation of a,b-unsaturated aldehydes", Phys. Chem. Chem. Phys., 2013, 15, 12048-12055.*
De Cola et al. (2006). Non-oxidative propane dehydrogenation over Pt—Zn-containing zeolites. Applied Catalysis A: General, 306, 85-97.
Kumar et al. (2009). The influence of pore geometry of Pt containing ZSM-5, Beta and SBA-15 catalysts on dehydrogenation of propane. Microporous and Mesoporous Materials, 126, 152-158.
Zhang et al. (2006). Propane dehydrogenation on PtSn/ZSM-5 catalyst: Effect of tin as a promoter. Catalysis Communications, 7, 860-866.

* cited by examiner

*Primary Examiner* — Elizabeth D Wood
(74) *Attorney, Agent, or Firm* — Caesar Rivise, PC

(57) ABSTRACT

The present invention relates to a zeolite catalyst for preparing light alkene by dehydrogenation of light alkane including a cocatalyst metal selected from tin (Sn), germanium (Ge), lead (Pb), gallium (Ga) and indium (In), and a preparation method of the same. The catalyst of the present invention is prepared by using the zeolite having a relatively high pore diameter, a structure of at least 12-membered ring, and a low acidity due to a $SiO_2/Al_2O_3$ ratio of at least 50, so that it can suppress the inactivation of a catalyst caused by pore clogging due to the formation of coke. Therefore the catalyst of the present invention can be effectively used as a catalyst for the preparation of light alkene by dehydrogenation of light alkane.

8 Claims, 1 Drawing Sheet

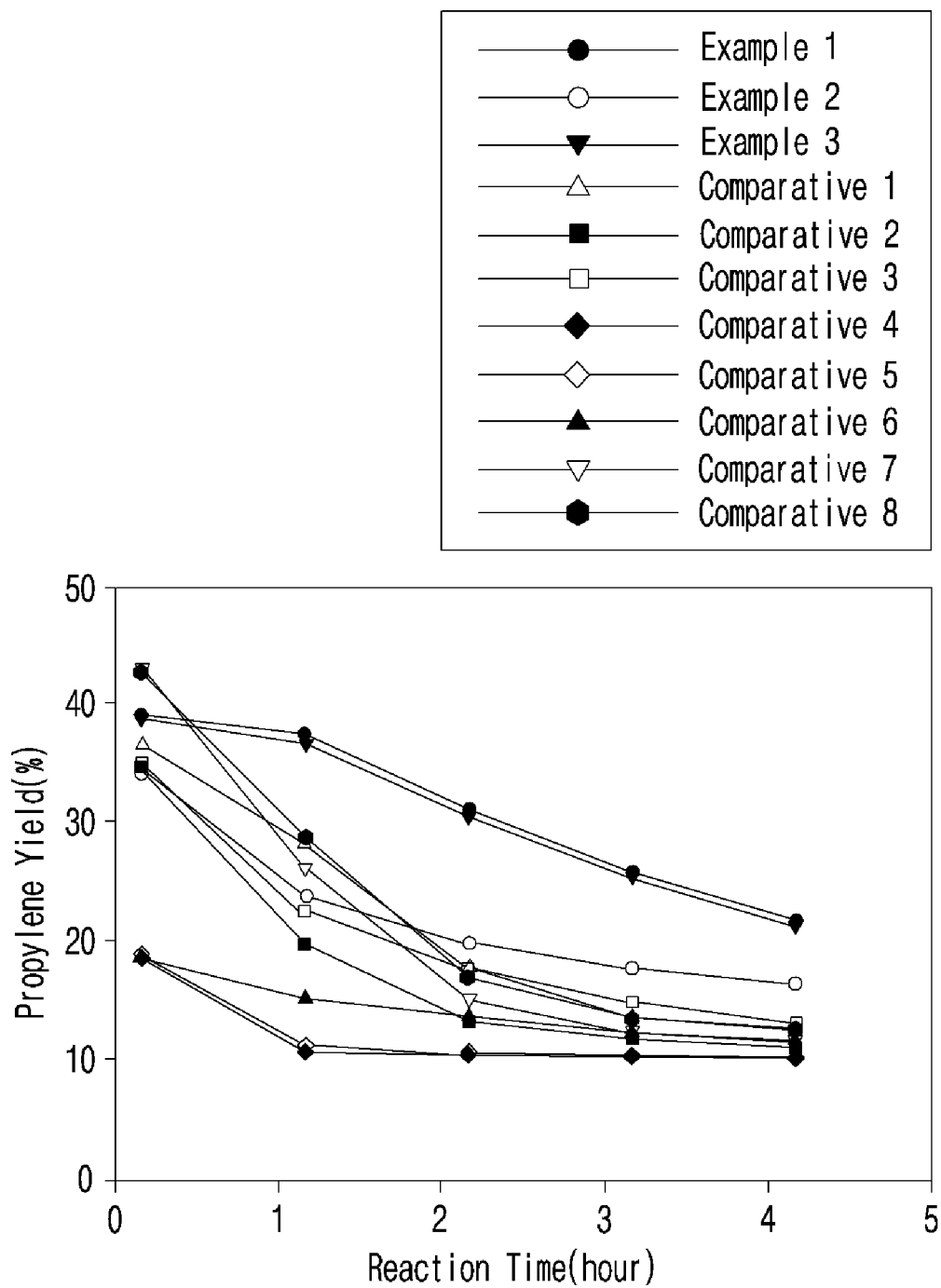

, # METAL-LOADED ZEOLITE CATALYST FOR DEHYDROGENATION OF LIGHT ALKANE AND PREPARATION METHOD THEREOF

BACKGROUND OF THE INVENTION

1. Field of the Invention

The present invention relates to a metal-loaded zeolite catalyst for dehydrogenation of light alkane and a preparation method thereof.

2. Description of the Related Art

Due to the recent development of shale gas, the price of light alkane, especially propane, is rapidly stabilized. Shale gas contains a large amount of light alkane gas such as ethane gas, propane gas, and butane gas. So, the process of dehydrogenation for preparing light alkene such as propylene is in the spotlight.

The dehydrogenation of light alkane gas, particularly propane, is performed at a high temperature over 550° C. Since the catalytic reaction of dehydrogenation is performed at the high temperature, side reactions such as pyrolysis and coke generation are accompanied. The degree of such side reactions is a key factor to determine the selectivity and activity of a catalyst. The coke generation, which is one of the side reactions, reduces the overall reaction conversion rate of a catalyst by blocking the contact with the reactants by covering the active metal on the catalyst with coke. As the coke generation progresses, the pore inlet in the catalyst is clogged, and the accessibility of the reactant is greatly reduced due to the active metal present in the pores, leading to the rapid deactivation of the catalyst.

Dehydrogenation catalysts can be divided into two groups according to the active metal component, which are chromium oxide catalysts and platinum catalysts.

In the case of the chromium oxide catalyst (U.S. Pat. No. 6,797,850), the deactivation rate of the catalyst according to the coke generation is high, and thus the regeneration must be frequently occurred. Therefore, the lifetime of the catalyst is relatively short, compared with that of the platinum catalyst, and the chromium oxide catalyst has environmental problems due to the toxicity of chromium itself.

When gamma-alumina (U.S. Pat. No. 6,756,515) is used as a support to load an active metal component, the possibility of side reaction increases due to the high acidity of the alumina support itself and the possibility of changes in alumina phase during the reaction is also high and the specific surface area is significantly reduced due to the high reaction temperature, indicating that the structural characteristics can be changed. Alpha-alumina (U.S. Pat. No. 6,486,370) lowers the dispersibility of the active metal due to the low specific surface area and reduces the overall active area, indicating that it shows a low catalytic activity.

Most of the patents related to dehydrogenation catalysts informed so far have dealt with alumina, silica or silica alumina mixture as a support. Zeolite has a large surface area and a high thermal stability. In particular, zeolite exhibits excellent acid catalytic properties, so that it has been widely used in various reactions such as cracking, isomerization, and dehydration. However, studies on the dehydrogenation have been limited.

PRIOR ART REFERENCE

Patent Reference (Patent Reference 1) U.S. Pat. No. 6,797,850
(Patent Reference 2) U.S. Pat. No. 6,756,515
(Patent Reference 3) U.S. Pat. No. 6,486,370

SUMMARY OF THE INVENTION

It is an object of the present invention to provide a metal-loaded catalyst for preparing light alkene from dehydrogenation of light alkane.

It is another object of the present invention to provide a preparation method of a metal-loaded catalyst for preparing light alkene.

It is also an object of the present invention to provide a preparation method of light alkene via the dehydrogenation of light alkane using the catalyst for preparing light alkene above.

The catalyst for preparing light alkene according to an example of the present invention contains zeolite having pores with a 12- or more ring structure; platinum; and a cocatalyst metal selected from the group consisting of tin (Sn), germanium (Ge), lead (Pb), gallium (Ga) and indium (In).

The said zeolite can have the ratio of $SiO_2/Al_2O_3$ of 50~1000.

The said zeolite can contain at least one of Beta zeolite and Y zeolite.

The content of the platinum above can be 0.05 to 1.5 weight % by the total weight of the catalyst.

The cocatalyst above can include tin (Sn).

The content of the cocatalyst above can be 0.05 to 2.0 weight % by the total weight of the catalyst.

The catalyst for preparing light alkene above can additionally include an alkali metal or an alkaline earth metal.

The preparation method of a catalyst for preparing light alkene according to an example of the present invention comprises the following steps:

calcinating the zeolite having pores with a 12- or more ring structure (step 1);

loading a cocatalyst selected from the group consisting of tin (Sn), germanium (Ge), lead (Pb), gallium (Ga) and indium (In) in the zeolite calcinated in step 1 (step 2); and loading platinum in the zeolite finished with step 2 above (step 3).

The preparation method of a catalyst for preparing light alkene according to another example of the present invention is to prepare light alkane through the dehydrogenation of light alkane by using the catalyst for preparing light alkene above.

The light alkane above can be selected from the group consisting of ethane, propane, and butane.

Advantageous Effect

The catalyst for preparing light alkene of the present invention is a catalyst for dehydrogenation of light alkane using the zeolite having a low acidity due to a high $SiO_2/Al_2O_3$ ratio of 50 to 1000, pores with a 12- or more ring structure, a large surface area, and an excellent thermal stability as a support. Since the catalyst of the present invention has a high dehydrogenation performance and high reaction stability due to the ability of delaying the deactivation caused by the coke generation, it can be effectively used as a catalyst for the dehydrogenation reaction.

BRIEF DESCRIPTION OF THE DRAWINGS

The application of the preferred embodiments of the present invention is best understood with reference to the accompanying drawings, wherein:

FIG. 1 is a graph illustrating the changes in propylene yield according to reaction time through the dehydrogenation of propane using the catalysts prepared in Examples 1~3 and Comparative Examples 1~8.

DESCRIPTION OF THE PREFERRED EMBODIMENTS

Hereinafter, the preferable embodiments of the present invention are described with the attached drawings. However, the embodiments of the present invention can be modified and altered in various ways and the present invention is not limited to the following illustration. It is well understood by those in the art who has the average knowledge on this field that the embodiments of the present invention are given to explain the present invention more precisely. Therefore, the shape and size of the elements in the drawings may be exaggerated for clarity of illustration and the elements indicated by the same mark in the drawings are the same elements. The factors showing similar function or activity are also indicated by the same mark in all the drawings. In addition, the inclusion of an element throughout the specification does not exclude other elements, but may include other elements, unless specifically stated otherwise.

Catalyst for Preparing Light Alkene

The catalyst for preparing light alkene according to an example of the present invention contains zeolite having pores with a 12- or more ring structure; platinum; and a cocatalyst selected from the group consisting of tin (Sn), germanium (Ge), lead (Pb), gallium (Ga) and indium (In).

If the ring structure of the zeolite is less than 12, there is a chance of clogging of pores or performance deterioration while the catalyst is in action because of too small pores. If the ring structures of the zeolite is more than 30, not only the synthesis of the zeolite itself is difficult but also the stability of the zeolite decreases, indicating that it may not be suitable as a catalyst support for promoting the dehydrogenation reaction of light alkane.

The said zeolite can have the ratio of $SiO_2/Al_2O_3$ of 50~1000.

If the ratio of $SiO_2/Al_2O_3$ is less than 50, side reactions are induced due to the high acidity of zeolite so that the efficiency of alkane dehydrogenation can be decreased. If the ratio of $SiO_2/Al_2O_3$ is higher than 1000, the post-treatment of zeolite is difficult or it may not be suitable as a catalyst support for promoting the dehydrogenation reaction of light alkane because the stability of the zeolite itself is reduced in that case. Even though the zeolite has a problem of side reactions due to the high acidity, the acidity can be controlled by regulating the ratio of $SiO_2/Al_2O_3$ in the zeolite. To inhibit such a side reaction as the coke generation caused by acid sites efficiently, the molar ratio of $SiO_2/Al_2O_3$ is preferably regulated to be 50~1000.

The ratio of $SiO_2/Al_2O_3$ in zeolite, in order for the catalyst containing the zeolite to promote the dehydrogenation of light alkane, is preferably 80~1000, 80~1000, 80~500, or 300~500.

The said zeolite can have a large surface area of about 400 to 800 $m^2/g$.

The said zeolite can contain at least one of Beta zeolite and Y zeolite.

The catalyst for preparing light alkene according to an example of the present invention preferably includes Beta zeolite and Y zeolite having the structure of BEA and FAU with at least 12- or more ring structures in order to inhibit the rapid deactivation of the catalyst caused by blocking the approach to the active metal in the pores due to zeolite pore clogging resulted from the coke generation, and more preferably includes Beta zeolite wherein all the pores are connected in three-dimensional channels.

The catalyst for preparing light alkene according to an example of the present invention can be a catalyst for the dehydrogenation of light alkane comprising a complex metal active component such as platinum and a cocatalyst metal for the dehydrogenation. So, the present invention provides a catalyst with increased reaction stability and improved dehydrogenation performance by delaying the deactivation caused by coke generation. The said zeolite can be functioning as a support to disperse the active metal component for the dehydrogenation reaction.

The active metal component above can include a complex metal active component such as platinum and a cocatalyst metal for the dehydrogenation reaction.

The content of the platinum above can be 0.05 to 1.5 weight % by the total weight of the catalyst.

If the content is less than 0.05 weight %, indicating that the ratio of an active ingredient is too low, the reaction activity is reduced. If the content is more than 1.5 weight %, the degree of dispersion becomes low and thereby side reactions are induced, resulting in the decrease of reaction performance.

The cocatalyst metal above is selected from the group consisting of tin (Sn), germanium (Ge), lead (Pb), gallium (Ga) and indium (In), and more preferably tin (Sn) herein.

The content of the cocatalyst above can be 0.05 to 2.0 weight % by the total weight of the catalyst.

If the content of the cocatalyst metal is less than 0.05 weight %, the effect of the cocatalyst is not observed, while if the content is more than 2.0 weight %, the platinum-metal alloy may be increased due to excessive amount of the cocatalyst metal component, resulting in the decrease of the catalytic activity.

The catalyst for preparing light alkene according to an example of the present invention can promote the dehydrogenation reaction of light alkane. The light alkane is preferably ethane, propane, or butane, and more preferably propane, but not always limited thereto.

Preparation Method of Catalyst for Preparing Light Alkene

The preparation method of a catalyst for preparing light alkene according to another example of the present invention comprises the following steps:

calcinating the zeolite having pores with a 12- or more ring structure (step 1);

loading a cocatalyst metal selected from the group consisting of tin (Sn), germanium (Ge), lead (Pb), gallium (Ga) and indium (In) in the zeolite calcinated in step 1 (step 2); and loading platinum in the zeolite finished with step 2 above (step 3).

Step 1 of the preparation method of a catalyst for preparing light alkene according to another example of the present invention is to calcinate the zeolite having pores with a 12- or more ring structure.

The zeolite above can include all the contents described in the catalyst for preparing light alkene according to an example of the present invention, so the description is omitted herein to avoid inconvenience of repeat.

The calcination can be performed in an air or atmospheric environment.

To impart the acid property to the zeolite above, zeolite is preferably calcinated at 500° C. or higher and if it includes ammonium ($NH_4^+$) as cations, it is preferred to replace ammonium ($NH_4^+$) with hydrogen ($H^+$). And the impurities are preferably eliminated.

The impurities in the zeolite are removed through the calcination step, so that the purity of the zeolite can be improved.

Step 2 of the preparation method of a catalyst for preparing light alkene according to another example of the present invention is to load a cocatalyst metal selected from the group consisting of tin (Sn), germanium (Ge), lead (Pb), gallium (Ga) and indium (In) in the zeolite calcinated in step 1.

A impregnation method can be used to load the cocatalyst metal in zeolite.

The method for loading the cocatalyst in zeolite is as follows: dissolving a precursor comprising the cocatalyst in an acid solution to prepare a precursor solvent and then loading the cocatalyst in zeolite using the prepared precursor solution, followed by drying.

Step 3 of the preparation method of a catalyst for preparing light alkene according to another example of the present invention is to load platinum in the zeolite finished with step 2 above.

An impregnation method can be used to load platinum in zeolite.

The method for loading platinum in zeolite is as follows: dissolving a precursor comprising platinum in an acid solution to prepare a precursor solvent and then loading platinum in zeolite using the prepared precursor solution, followed by drying.

Preparation Method of Light Alkene

The preparation method of light alkene according to another example of the present invention comprises preparing light alkene by dehydrogenation of light alkane using the catalyst for preparing light alkene according to an example of the present invention.

The catalyst for preparing light alkene used in the preparation method of light alkene of the invention can include all the contents described for the catalyst for preparing light alkene according to an example of the present invention, so the description about the catalyst herein is omitted herein to avoid inconvenience of repeat The preparation method of light alkene according to another example of the present invention can provide the light alkene with high light alkane conversion, high light alkene selectivity and high yield by inhibiting such a side reaction as coke generation and by controlling the acidity of the catalyst.

The light alkane above can be selected from the group consisting of ethane, propane, and butane.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Preparation of Pt/Sn/Beta ($SiO_2/Al_2O_3$=300) Catalyst

A catalyst was prepared by loading Sn and Pt in Beta zeolite ($SiO_2/Al_2O_3$ molar ratio: 300) in that order by the following method. At this time, the loading content of Sn was 0.22 weight % by the total weight of the catalyst and the loading content of Pt was 0.82 weight %.

Step 1: Calcinating Zeolite

The Beta zeolite (Zeolyst, CP811C-300) with the molar ratio of $SiO_2/Al_2O_3$ of 300 was calcinated in an air atmosphere at 550° C. for 6 hours to convert ammonium ($NH_4^+$) cations to hydrogen ($H^+$) and the impurities were removed, which was used as a support for the synthesis of a catalyst.

Step 2: Loading Cocatalyst Metal

A impregnation method was used to load Sn in the zeolite prepared in step 1.

0.0359 g of tin chloride ($SnCl_2$, >99%, Sigma), 0.2778 g of hydrochloric acid (HCl, >36%, Samchun), and 0.0384 g of nitric acid ($HNO_3$, 65%, Duksan) were dissolved in 100 g of distilled water to prepare a precursor solution.

10 g of the Beta zeolite prepared in step 1 was dispersed in the precursor solution, followed by stirring in a rotary evaporator at room temperature for 1.5 hours. Water was removed by evaporation drying at 80° C. for 1.5 hours under reduced pressure. Additional drying was performed in an oven at 105° C. for 15 hours, leading to complete drying. Calcination was performed at 700° C. for 3 hours in an air atmosphere, leading to the preparation of the Beta zeolite loaded with Sn.

Step 3: Loading Platinum

Platinum was loaded in Beta zeolite by the similar manner as described for the loading of tin in step 2.

0.1660 g of chloroplatinic acid hexahydrate ($H_2PtCl_6 \cdot 6H_2O$, 99.95%, Aldrich), 0.1042 g of hydrochloric acid (HCl, >36%, Samchun), and 0.0289 g of nitric acid ($HNO_3$, 65%, Duksan) were dissolved in 100 g of distilled water to prepare a precursor solution.

7.5 g of the tin-loaded Beta zeolite prepared in step 2 was dispersed in the precursor solution, followed by stirring in a rotary evaporator at room temperature for 1.5 hours. Water was removed by evaporation drying at 80° C. for 1.5 hours under reduced pressure. Additional drying was performed in an oven at 105° C. for 15 hours, leading to complete drying. Calcination was performed at 600° C. for 3 hours in an air atmosphere, leading to the preparation of the Beta zeolite catalyst loaded with platinum (Pt) and a tin (Sn) cocatalyst.

EXAMPLE 2

Preparation of Pt/Sn/Y ($SiO_2/Al_2O_3$=80) Catalyst

A Y zeolite catalyst loaded with platinum (Pt) and a tin (Sn) cocatalyst was prepared by the same manner as described in Example 1 except that CBV901 Y zeolite ($SiO_2/Al_2O_3$ molar ratio: 80, Zeolyst) was used instead of the Beta zeolite used in Example 1.

EXAMPLE 3

Preparation of Pt/Sn/Beta ($SiO_2/Al_2O_3$=710) Catalyst

A Beta zeolite catalyst loaded with platinum (Pt) and a tin (Sn) cocatalyst was prepared by the same manner as described in Example 1 except that the $SiO_2/Al_2O_3$ molar ratio in the Beta zeolite was controlled to be 710 by inducing dealumination of the Beta zeolite ($SiO_2/Al_2O_3$ molar ratio: 300).

Hereinafter, the dealumination process is described in detail.

Step 1: CP811C-300 Beta zeolite ($SiO_2/Al_2O_3$ molar ratio: 300) was calcinated at 550° C. for 6 hours in an air atmosphere to eliminate impurities.

Step 2: The Beta zeolite was dealuminated by acid treatment to have a desired $SiO_2/Al_2O_3$ molar ratio.

100 mL of 1 M nitric acid ($HNO_3$) solution and 2 g of the calcinated Beta zeolite were mixed at room temperature for 12 hours and thereby aluminum in the zeolite lattice was properly eliminated. At this time, the acid could be in various forms and was not limited to nitric acid.

Step 3: After the mixing above, the aluminum component removed from the zeolite lattice was eliminated by washing with hot water three to four times, followed by centrifugation. Finally, the dealuminated zeolite was prepared by drying the sample in a 120° C. oven for 12 hours.

EXAMPLE 4

Preparation of K/Pt/Sn/Beta ($SiO_2/Al_2O_3$=300) Catalyst

A catalyst prepared by loading tin (Sn), platinum (Pt), and potassium (K) in Beta zeolite ($SiO_2/Al_2O_3$ molar ratio: 300) in that order was prepared by the following method. At this time, the loading content of Sn was 0.22 weight % by the total weight of the catalyst, the loading content of Pt was 0.82 weight %, and the loading content of K was 0.74 weight %.

Step 1: Calcinating Zeolite

The Beta zeolite (Zeolyst, CP811C-300) with the molar ratio of $SiO_2/Al_2O_3$ of 300 was calcinated at 550° C. for 6 hours in an air atmosphere to convert ammonium ($NH_4^+$) cations to hydrogen ($H^+$) and the impurities were removed, which was used as a support for the synthesis of a catalyst.

Step 2: Loading Cocatalyst Metal

A impregnation method was used to load Sn in the zeolite prepared in step 1.

0.0359 g of tin chloride ($SnCl_2$, >99%, Sigma), 0.2778 g of hydrochloric acid (HCl, >36%, Samchun), and 0.0384 g of nitric acid ($HNO_3$, 65%, Duksan) were dissolved in 100 g of distilled water to prepare a precursor solution.

10 g of the Beta zeolite prepared in step 1 was dispersed in the precursor solution, followed by stirring in a rotary evaporator at room temperature for 1.5 hours. Water was removed by evaporation drying at 80° C. for 1.5 hours under reduced pressure. Additional drying was performed in an oven at 105° C. for 15 hours, leading to complete drying. Calcination was performed at 700° C. for 3 hours in an air atmosphere, leading to the preparation of the Beta zeolite loaded with Sn.

Step 3: Loading Platinum

Platinum was loaded in Beta zeolite by the similar manner as described for the loading of tin in step 2.

0.1660 g of chloroplatinic acid hexahydrate ($H_2PtCl_6 \cdot 6H_2O$, 99.95%, Aldrich), 0.1042 g of hydrochloric acid (HCl, >36%, Samchun), and 0.0289 g of nitric acid ($HNO_3$, 65%, Duksan) were dissolved in 100 g of distilled water to prepare a precursor solution.

7.5 g of the tin-loaded Beta zeolite prepared in step 2 was dispersed in the precursor solution, followed by stirring in a rotary evaporator at room temperature for 1.5 hours. Water was removed by evaporation drying at 80° C. for 1.5 hours under reduced pressure. Additional drying was performed in an oven at 105° C. for 15 hours, leading to complete drying. Calcination was performed at 600° C. for 3 hours in an air atmosphere, leading to the preparation of the Beta zeolite catalyst loaded with platinum (Pt) and a tin (Sn) cocatalyst.

Step 4: Loading Alkali Metal or Alkaline Earth Metal

Potassium was loaded in Beta zeolite by the similar manner as described for the loading of tin in step 2.

0.0976 g of potassium nitrate ($KNO_3$, 99%, Aldrich) and 0.0792 g of hydrochloric acid (HCl, >36%, Samchun) were dissolved in 100 g of distilled water to prepare a precursor solution.

5 g of the platinum and tin-loaded Beta zeolite prepared in step 3 was dispersed in the precursor solution, followed by stirring in a rotary evaporator at room temperature for 1.5 hours. Water was removed by evaporation drying at 80° C. for 1.5 hours under reduced pressure. Additional drying was performed in an oven at 105° C. for 15 hours, leading to complete drying. Calcination was performed at 600° C. for 3 hours in an air atmosphere, leading to the preparation of the Beta zeolite catalyst loaded with potassium (K), platinum (Pt), and tin (Sn).

COMPARATIVE EXAMPLE 1

Preparation of Pt/Sn/Beta ($SiO_2/Al_2O_3$=38) Catalyst

A Beta zeolite catalyst loaded with platinum (Pt) and a tin (Sn) cocatalyst was prepared by the same manner as described in Example 1 except that CP814C Beta zeolite ($SiO_2/Al_2O_3$ molar ratio: 38, Zeolyst) was used instead of the Beta zeolite ($SiO_2/Al_2O_3$ molar ratio: 300) used in Example 1.

COMPARATIVE EXAMPLE 2

Preparation of Pt/Sn/Beta ($SiO_2/Al_2O_3$=25) Catalyst

A Beta zeolite catalyst loaded with platinum (Pt) and a tin (Sn) cocatalyst was prepared by the same manner as described in Example 1 except that CP814E Beta zeolite ($SiO_2/Al_2O_3$ molar ratio: 25, Zeolyst) was used instead of the Beta zeolite ($SiO_2/Al_2O_3$ molar ratio: 300) used in Example 1.

COMPARATIVE EXAMPLE 3

Preparation of Pt/Sn/Y ($SiO_2/Al_2O_3$=30) Catalyst

A Y zeolite catalyst loaded with platinum (Pt) and a tin (Sn) cocatalyst was prepared by the same manner as described in Example 1 except that CBV720 Y zeolite ($SiO_2/Al_2O_3$ molar ratio: 30, Zeolyst) was used instead of the Beta zeolite used in Example 1.

COMPARATIVE EXAMPLE 4

Preparation of Pt/Beta ($SiO_2/Al_2O_3$=300) Catalyst

A Beta zeolite catalyst loaded with platinum (Pt) only was prepared by the same manner as described in Example 1 except that there was no step of loading the cocatalyst metal of step 2 in Example 1.

COMPARATIVE EXAMPLE 5

Preparation of Pt/Y ($SiO_2/Al_2O_3$=80) Catalyst

A Y zeolite catalyst loaded with platinum (Pt) only was prepared by the same manner as described in Example 1 except that the zeolite ($SiO_2/Al_2O_3$ molar ratio: 80, Zeolyst)

was used instead of the Beta zeolite used in Example 1 and there was no step of loading the cocatalyst metal of step 2.

COMPARATIVE EXAMPLE 6

Preparation of Pt/Sn/ZSM-5 ($SiO_2/Al_2O_3$=280) Catalyst

A ZSM-5 zeolite catalyst loaded with platinum (Pt) and a tin (Sn) cocatalyst was prepared by the same manner as described in Example 1 except that CBV28014 ZSM-5 zeolite ($SiO_2/Al_2O_3$ molar ratio: 280, Zeolyst) was used instead of the Beta zeolite used in Example 1.

COMPARATIVE EXAMPLE 7

Preparation of Pt/Sn/θ-$Al_2O_3$ Catalyst

A θ-$Al_2O_3$ catalyst loaded with platinum (Pt) and a tin (Sn) cocatalyst was prepared by the same manner as described in Example 1 except that the θ-$Al_2O_3$ prepared by calcinating Catapal B boehmite (Sasol) at 1050° C. for 6 hours in an air atmosphere was used instead of the Beta zeolite used in Example 1.

COMPARATIVE EXAMPLE 8

Preparation of Pt/Sn/γ-$Al_2O_3$ Catalyst

A γ-$Al_2O_3$ catalyst loaded with platinum (Pt) and a tin (Sn) cocatalyst was prepared by the same manner as described in Example 1 except that the γ-$Al_2O_3$ prepared by calcinating Catapal B boehmite (Sasol) at 650° C. for 6 hours in an air atmosphere was used instead of the Beta zeolite used in Example 1.

EXPERIMENTAL EXAMPLE 1

Dehydrogenation of Propane using Metal-loaded Zeolite Catalyst

Propane dehydrogenation was performed by using a continuous fixed bed reactor in order to investigate the yield of propylene generated through the dehydrogenation of propane using the catalysts prepared in Examples 1~4 and Comparative Examples 1~8.

The catalysts (0.5 g) prepared in Examples 1~4 and Comparative Examples 1~8 were loaded in a quartz reactor and pretreated at 620° C. under atmospheric pressure for 2 hours while flowing hydrogen and nitrogen at the flow rate of 50 SCCM.

After the pretreatment, dehydrogenation was performed by injecting gaseous propane ($C_3H_8$, 99.99%), the reactant, at the flow rate of 25 SCCM (weight hour space velocity, WHSV=6 $hr^{-1}$) while maintaining the reaction temperature and pressure at 620° C. under atmospheric pressure.

The composition of the gas product obtained after the reaction was analyzed using gas chromatography (GC) connected to the reaction system, from which the propane conversion and the selectivity and yield of propylene were calculated.

Propane dehydrogenation was performed using the catalysts prepared in Examples 1~4 and Comparative Examples 1~8. The changes of the yield of propylene over the reaction time are shown in FIG. 1. And the reaction results after 4 hours of the reaction are shown in Table 1.

TABLE 1

| | Loading metal | Support | $SiO_2/Al_2O_3$ molar ratio | Propane conversion rate (%) | Propylene selectivity (%) | Propylene yield (%) |
|---|---|---|---|---|---|---|
| Example 1 | Pt/Sn | Beta | 300 | 33.0 | 65.5 | 21.6 |
| Example 2 | Pt/Sn | Y | 80 | 28.2 | 58.1 | 16.4 |
| Example 3 | Pt/Sn | Beta | 710 | 32.1 | 66.3 | 21.3 |
| Example 4 | K/Pt/Sn | Beta | 300 | 50.5 | 79.9 | 40.4 |
| Comparative Example 1 | Pt/Sn | Beta | 38 | 24.0 | 50.7 | 12.2 |
| Comparative Example 2 | Pt/Sn | Beta | 25 | 22.9 | 47.6 | 10.9 |
| Comparative Example 3 | Pt/Sn | Y | 30 | 27.0 | 48.1 | 13.0 |
| Comparative Example 4 | Pt | Beta | 300 | 23.1 | 43.1 | 10.0 |
| Comparative Example 5 | Pt | Y | 80 | 21.8 | 46.3 | 10.1 |
| Comparative Example 6 | Pt/Sn | ZSM-5 | 280 | 34.7 | 33.1 | 11.5 |
| Comparative Example 7 | Pt/Sn | θ-$Al_2O_3$ | | 0 | 23.3 | 11.5 |
| Comparative Example 8 | Pt/Sn | γ-$Al_2O_3$ | | 0 | 25.7 | 12.4 |

As shown in Table 1 and FIG. 1, the catalysts loaded with platinum and a tin cocatalyst in the Beta and Y zeolites having $SiO_2/Al_2O_3$ ratio of at least 50 and comparatively large pores with a 12- or more ring structure (Examples 1, 2, and 3) maintained as high propylene yield as 21.6%, 16.4%, and 21.3% after 4 hours of the reaction. In the meantime, the hydrogenation catalyst using the conventional alumina support (Comparative Examples 7 and 8) showed the maximum propylene yield of 12.4%.

Therefore, it was confirmed that the propylene yield by the catalysts of the present invention was significantly increased at least by 74%, 32%, and 72%. Those Beta zeolite catalysts having high $SiO_2/Al_2O_3$ ratios of 300 and 710 (Examples 1 and 3) showed similar reaction performance.

The catalysts loaded with platinum and a tin cocatalyst in the Beta and Y zeolites having $SiO_2/Al_2O_3$ molar ratio of less than 50 and in the ZSM-5 zeolite having comparatively small pores with a 10-ring structure (Examples 1, 2, 3, and 6) showed the similar or lower propylene yield than those of the conventional alumina loaded catalysts.

Further, in the case of the Beta and Y zeolite catalysts loaded with platinum alone without tin (Comparative Examples 4 and 5), the yield of propylene was remarkably lower than that of the conventional alumina loaded catalysts.

Therefore, the catalyst of the present invention using the zeolite having a low acidity due to the high $SiO_2/Al_2O_3$ ratio of at least 50 and relatively big pores with a 12- or more ring structure as a support and loaded with a complex metal active component such as platinum and a cocatalyst metal for the conventional dehydrogenation reaction well known to those in the art can inhibit the deactivation of the catalyst caused by blocking the approach to the active metal in the pores due to pore clogging resulted from the coke generation and can maintain a high propylene yield in the course of propane dehydrogenation reaction, so that the catalyst of the invention can be effectively used as a catalyst for the preparation of light alkene by dehydrogenation of light alkane.

The Beta zeolite catalyst loaded with potassium, platinum, and tin (Example 4) according to an example of the present invention demonstrated a significantly high propylene yield of 40.4% after 4 hours of the reaction. Even after 24 hours of the reaction, the propylene yield was maintained as high as at least 30%.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A catalyst for preparing a light alkene comprising:
    a beta zeolite comprising pores with a 12-membered or more than 12-membered ring structure;
    platinum; and
    tin (Sn), wherein the beta zeolite comprises $SiO_2/Al_2O_3$ at a ratio of 300-1000 and the catalyst is effective for preparing the light alkene by dehydrogenation of a light alkane.

2. The catalyst for preparing a light alkene according to claim 1, wherein a content of the platinum is 0.05-1.5 weight % based on a total weight of the catalyst.

3. The catalyst for preparing a light alkene according to claim 1, wherein a content of the tin (Sn) is 0.05-2.0 weight % based on a total weight of the catalyst.

4. The catalyst for preparing a light alkene according to claim 1, wherein the catalyst for dehydrogenation of light alkane additionally comprises an alkali metal or an alkaline earth metal.

5. A method for preparing the catalyst of claim 1 comprising the following steps:
    calcinating a beta zeolite comprising pores with a 12-membered or more than 12-membered ring structure (step 1);
    loading tin (Sn) in the zeolite calcinated in step 1(step 2); and
    loading platinum in the beta zeolite finished with step 2 above (step 3),
    wherein the beta zeolite comprises $SiO_2/Al_2O_3$ at a ratio of 300-1000, and the catalyst is effective for preparing the light alkene by dehydrogenation of the light alkane.

6. A light alkene preparation method comprising dehydrogenation of a light alkane comprising contacting the light alkane with the catalyst of claim 1.

7. The light alkene preparation method according to claim 6, wherein the light alkane is a member selected from the group consisting of ethane, propane, and butane.

8. A method of preparing propylene, comprising contacting a light propane with the catalyst of claim 1 to dehydrogenate the light propane, wherein a reaction temperature is 550-700° C. and a reaction pressure is 0.1-10 absolute atmospheric pressure.

* * * * *